United States Patent [19]

St. John

[11] Patent Number: 4,595,713
[45] Date of Patent: Jun. 17, 1986

[54] MEDICAL PUTTY FOR TISSUE AUGMENTATION

[75] Inventor: Kenneth St. John, Tracy, Calif.

[73] Assignee: Hexcel Corporation, San Francisco, Calif.

[21] Appl. No.: 693,162

[22] Filed: Jan. 22, 1985

[51] Int. Cl.⁴ ............... A61K 31/23; A61K 31/74; A61K 35/32

[52] U.S. Cl. .................... 523/105; 424/14; 623/10; 623/13; 523/109; 523/112; 523/113; 523/114; 523/115; 525/415; 528/354; 623/16

[58] Field of Search ............... 424/14; 514/801; 3/1, 3/1.91; 523/105, 109, 112, 113, 114, 115; 525/415; 528/354

[56] References Cited

U.S. PATENT DOCUMENTS

| | | | |
|---|---|---|---|
| 3,919,773 | 11/1975 | Freeman | 433/175 |
| 3,949,073 | 4/1976 | Daniels et al. | 424/177 |
| 4,045,418 | 8/1977 | Sinclair | 528/357 |
| 4,057,537 | 11/1977 | Sinclair | 528/354 |
| 4,129,470 | 12/1978 | Homsy | 3/1.91 |
| 4,137,921 | 2/1979 | Okuzumi et al. | 128/335.5 |
| 4,243,775 | 1/1981 | Rosensaft et al. | 128/335.5 |
| 4,273,920 | 6/1981 | Nevin | 528/354 |
| 4,279,249 | 7/1981 | Vert et al. | 128/335.5 |
| 4,347,234 | 8/1982 | Wahlig et al. | 128/335.5 |
| 4,424,208 | 1/1984 | Wallace et al. | 424/177 |
| 4,439,420 | 3/1984 | Mattei et al. | 424/78 |
| 4,440,750 | 4/1984 | Glowacki et al. | 424/95 |
| 4,440,789 | 4/1984 | Mattei et al. | 528/354 |
| 4,443,430 | 4/1984 | Mattei et al. | 528/354 |

FOREIGN PATENT DOCUMENTS 2849785  5/1979  Fed. Rep. of Germany ...... 525/415

Primary Examiner—Ronald W. Griffin
Attorney, Agent, or Firm—Oblon, Fisher, Spivak, McClelland & Maier

[57] ABSTRACT

A medical implant useful in the regeneration of soft and hard connective tissue, such as cartilage and bone, is disclosed which comprises a copolymer of a major amount of epsilon caprolactone and a minor amount of lactide. Where regeneration of bone tissue, in particular, is desired, the copolymer may further include osteogenic material in powdered or particulate form. If soft tissue regeneration is desired, the copolymer may include chopped carbon fiber. A mass of the copolymer, optionally including additives, may be molded by hand by heating the polymer to a temperature of 115°–160° F., by, for example, immersion in hot water. The mass is then molded to the void to be filled or shape the regenerated tissue is desired to assume, and implanted in the patient. The mass is gradually replaced by regenerated tissue.

15 Claims, No Drawings

MEDICAL PUTTY FOR TISSUE AUGMENTATION

BACKGROUND OF THE INVENTION

1. Field of the Invention

This invention relates to a moldable putty for use in medical applications for the augmentation of the replacement of hard and soft tissue. More specifically, this invention relates to a composite comprised of a polymer that is moldable at "hot water" temperatures, retains its shape at temperatures substantially below that range, and may include tissue growth augmentation materials.

2. Background of the Prior Art

It has long been known that the replacement or regeneration of supportive and connective tissue, particularly hard tissue such as bone materials, may be augmented by the presence or application of various organic and inorganic materials. Thus, U.S. Pat. No. 4,440,750, describes in detail a wide number of compounds found to be osteogenic, and describes a method and preparation for introducing such osteogenic materials where it is necessary to enhance or promote bone regeneration, such as in the case, of genetic disorders and traumatic injury.

Similarly, a large number of tissue augmentation compositions are known, that comprise soft or moldable polymeric materials, which are designed to occupy the space where tissue regeneration is desired, and eventually be replaced by the hard or soft regenerated tissue, such as cartilage or bone. Among the references directed to such invention are U.S. Pat. Nos. 4,424,208 and 4,347,234. The latter, in particular, describes a collagen-based shaped mass which may include osteogenic material, such as tricalcium phosphate. The implant material of both U.S. Pat. Nos. 4,424,208 and 4,347,234 is based on collagen in a binder to form a polymeric mass.

A similar material is provided through an alternative approach in U.S. Pat. No. 3,949,073. That patent describes a collagen-based solution which may be injected or implanted into the desired location, and immediately polymerized into a stable mass upon injection. The reference also suggests the use of tissue augmentation materials in addition to the collagen polymer.

A different approach to the replacement of bone tissue is taken in U.S. Pat. No. 3,919,773, which is directed to a bone replacement, or implant, particularly designed for use in dental or oral surgery, where a socket is exposed after tooth extraction, or an similar void is formed in dental bone. Accordingly, a polymerizable material, comprised, in contrast to U.S. Pat. No. 3,949,073, of synthetic polymers, is injected into the socket and rapidly polymerizes therein, to form a hardened, permanent fixture. To enhance subsequent tissue connection, but not replacement, to the implant, the material, prior to polymerization, is provided with discrete particles that are soluble in body fluids commonly encountered in the oral cavity. When these particles are dissolved, the implant is made porous, which enhances the connection of connective tissue thereto.

Also generally known in the art are purely synthetic polymers useful, in general, as surgical articles or devices, owing to their complete bioabsorbability. Thus, U.S. Pat. No. 4,243,775 describes a polymer based on lactide and glycolide, which, when polymerized, is designed as a medical suture, or similar sterile surgical article. However, the polymer of the reference is not moldable, and is not suggested as being suitable for the enhancement of, or replacement by, connective tissue.

Other related art also includes a variety of hemostatic materials, designed to control osseous hemorrhage, particularly in the case of orthopedic surgery or the like. Several different compositions are generally described in U.S. Pat. Nos. 4,439,420; 4,440,789 and 4,443,430. Although these compositions are useful in the healing process, and a necessary adjunct to surgical or traumatic injury to bone and similar connective tissue, they do not serve as "scaffolds" or similar basis for the replacement of the implant by regenerated tissue, nor do they substantially promote to the regeneration of that tissue.

All of the above-described medical articles and compositions suffer from one or more disadvantages in the provision of a medical putty which may be used as a temporary form for the augmentation of hard or soft connective tissue, both by replacement of the implant with regenerated tissue, and delivering an osteogenic material. Those compositions which are not moldable prior to insertion in the body of the patient present the extreme problem that the space, gap or void cannot be completely filled, or the scaffold cannot be designed or molded in the desired shape for eventual replacement by hard or soft tissue. This is particularly true of compositions designed to be polymerizable in situ, which offer only the possibility of filling the entire void or cavity with the implant.

Although the compositions based on collagen and including osteogenic materials, and designed to be molded outside the body, such as those of U.S. Pat. No. 4,347,234, present an alternative to the in situ polymerization methods, the reliance on a collagen-based polymer presents its own problems. Specifically, collagen is, although generally biocompatible, not completely biodegradable or resorbable, such that the implant remains for a long period of time in the wound area, being surrounded, but not absorbed, by the regenerating tissue. Additionally, collagen, being an organic substance principally derived from bovines, presents potentially serious allergenic reaction problems, and general difficulties with the patient's immune system. Further, it is difficult to insure the sterility of collagen, and the storage requirements associated therewith are quite extensive, and expensive. A further disadvantage presented by the use of collagen or collagen-based polymers is the moldability of the polymer. Although it is desirable for the polymer to be moldable outside the body, once inserted, the polymer should be preferably be resistant to permanent changes in shape through applied pressure, particularly where oral or dental surgery is involved. Thus, after implantation or substitution for mandibular or maxillary bone loss during oral surgery, it may be desirable or necessary for the patient to resume chewing, etc. The pressure and stress applied by these activities will deform an implant that remains moldable after implantation, and destroy, or at least detract from, the value and utility of the implanted article.

Accordingly, there continues to be a need for a stable but moldable implant material suitable for use in soft and hard tissue regeneration and replacement.

SUMMARY OF THE INVENTION

It is an object of this invention to provide an implant material suitable for the regeneration and replacement of soft and hard connective tissue.

It is a further object of this invention to provide an implant material which is moldable under temperatures that may be achieved in an operating room or medical environment, but remain stable during and after implantation.

It is yet another object of this invention to provide a material which is biocompatible and bioabsorbable, and may be replaced by regenerating connective tissue.

These and other objects more fully illuminated hereinbelow are achieved by the provision of an implant material which is comprised of a copolymer of lactide and epsilon caprolactone which, where regeneration of bone tissue is desired, further comprises an osteogenic material. The copolymer should generally be comprised of a major amount of epsilon caprolactone and a minor amount of lactide. Preferred ranges are from 60–95% epsilon caprolactone and 40–5% lactide. A particularly preferred embodiment contemplates a 75%/25% epsilon caprolactone/lactide mixture.

As osteogenic materials, there are contemplated the materials generally known in the art, such as those described in the afore-referenced U.S. Pat. No. 4,440,750, and, specifically, B-tricalcium phosphate, hydroxyapetite, alumino-calcium-phosphorous oxide (ALCAP), allograft or autogenous bone chips, or demineralized bone. Similar powdered or particulate materials intended for augmentation, stimulation or replacement of hard tissues would also be suitable.

The moldable polymer itself, without fillers, is useful as a putty which may be molded by hand, and occupy the void created, and thereafter progressively replaced by soft tissue.

In a further embodiment, the implant polymer may further comprise chopped carbon fiber. Carbon fiber is known to improve the regeneration of connective tissue in particular, improving its orientation and accelerating its growth. This, of course, should be distinguished from embodiments where long strands of carbon fiber are inserted with a coating to serve as an artificial tendon or ligament.

As a general guideline, fillers or osteogenic material may be incorporated in the implant up to about 50% by weight, without effecting the moldability or utility of the implant.

DETAILED DESCRIPTION OF THE INVENTION

The epsilon caprolactone/lactide copolymer employed in the implant of this invention is broadly disclosed and specifically described and claimed in U.S. patent application Ser. No., 491,927, filed May 5, 1983 and copending herewith. The pertinent disclosure thereof is incorporated herein by reference. Although the polymer, per se, does not constitute the entire invention, its characteristics are of sufficient import herein that its preparation is described below.

The polymer of the present invention is a copolymer of a lactide and epsilon caprolactone. The proportions of lactide and epsilon caprolactone can vary over a considerable range, so long as the epsilon caprolactone is present in the mixture of lactide and epsilon caprolactone, which is reacted to form the copolymer, in major amount. Preferably, the concentration of epsilon caprolactone in the mixture of lactide and epsilon caprolactone which is reacted to form the copolymer is in the range of about 60 to about 95 weight percent, based on the total weight of the mixture. The concentration of lactide in the mixture of lactide and epsilon caprolactone which is reacted to form the copolymer is in the range of about 40 to 5 weight percent, based on the total weight of the mixture. Most preferably, a mixture of about 75 weight percent epsilon caprolactone and about 25 weight percent of lactide is used to prepare the desired copolymer which is tough, having excellent elongation, of high tensile strength, and of a weight average molecular weight of about 200,000–500,000.

The lactide of the present invention corresponds to the general formula (I)

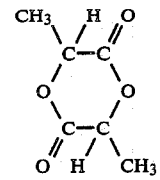

The lactide employed in accordance with the present invention can be optically active, e.g., L-(−)-lactide, or optically inactive, e.g., D,L-lactide. The L-(−)-lactide, which is a cyclic dimer of L-(+)-lactic acid, is commercially available. L-(−)-lactide is a white powder having a molecular weight of 144. If desired, commercially available L-(−)-lactide can be purified by recrystallization from anhydrous methyl isobutyl ketone, ethyl acetate or acetone. The snow-white crystals of L-(−)-lactide melt at about 95°–98° C. D,L-lactide is a cyclic dimer of D,L-lactic acid and is commercially available. D,L-lactide frequently comprises a mixture of D,D-, L,L- and D,L-lactide. Accordingly, when used herein, the term "D,L-lactide" is intended to include D,L-lactide andmixtures thereof with D,D- and/or L,L-lactide. D,L-lactide is a white powder having a molecular weight of 144. As with the L-(−)-lactide, commercially available D,L-lactide can be purified by conventional means, i.e., recrystallization from anhydrous methyl isobutyl ketone, ethyl acetate or acetone. The snow-white crystals obtainable melt at about 115°–129° C.

The epsilon caprolactone of the present invention corresponds to the general formula (II)

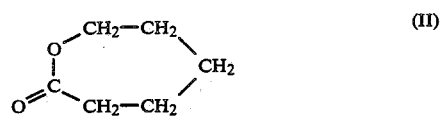

The epsilon caprolactone employed in accordance with the present invention is commercially available. Commercially available epsilon caprolactone can be purified by vacuum distillation, i.e., collecting that portion boiling at 56°–57° C./0.4 torr. Epsilon caprolactone is water-white with a single gas chromatography peak.

In preparing the lactide/epsilon caprolactone copolymer in accordance with this invention, it is preferred to carry out the reaction at atmospheric pressure in the liquid phase (either as a melt or in an inert liquid diluent) in the presence of a catalyst, blanketed by an inert gas such as, for example, nitrogen. The copolymers can also be prepared in a closed, evacuated vessel. If the polymerization is conducted in the presence of air, discoloration occurs along with a resulting degradation of polymer properties. The process can be carried out at any temperature above the melting point of the lactide, preferably, 10° C. above the lactide melting point. However, temperatures about 200° C. are undesirable because of the tendency of the copolymer to degrade. Temperatures below the melting point of the lactide can be used, if the reactants are dispersed or dissolved in an inert liquid, however, the use of lower temperatures prolongs the reaction and may result in less desirable polymers. Increasing the temperature of the reaction within the range from the melting point of the lactide to 200° C., generally increases the speed of the polymerization. Preferably, the mixture of lactide and epsilon caprolactone is reacted at a temperature of about 140°-150° C.

The catalysts employed in accordance with the present invention are metallic esters of carboxylic acids. Preferably, the carboxylic acid contains up to 18 carbon atoms. Examples of such acids are formic, acetic, propionic, butyric, valeric, caproic, caprylic (octoic), pelargonic, capric, lauric, myristic, palmitic, stearic, and benzoic acids. Preferred esters are the tin and zinc esters of carboxylic acids contained up to 18 carbon atoms. Good results have been obtained with stannous octoate and zinc octoate.

The catalyst concentration is preferably in the range of about 0.01 to about 1.0 percent by weight based on the total weight of the lactide and epsilon caprolactone. Good results have been obtained using catalyst concentration in the range of about 0.02 to about 0.03 percent by weight. The exact amount of catalyst in any particular case depends to a large extent upon the catalyst employed and the operating variables including time, temperature and pressure.

The reaction time, in most instances, is governed by the other reaction variables, e.g., temperature, pressure, catalyst, amount of catalyst, and whether a liquid vehicle is employed. In general, the reaction time will be in the range of hours to days, depending upon the particular set of conditions which are employed. For example, it takes at least 48 hours to complete a bulk polymerization reaction at atmospheric pressure and 140° C. when the catalyst concentration employed is about 0.02 percent by weight.

The polymerization is always carried out until no further reaction is detected which can be easily determined by monitoring the percent conversion of monomeric reactants versus reaction time, for example, using thermogravimetric analysis (TGA).

In general, it is preferred to conduct the polymerization in the absence of impurities which contain active hydrogen since the presence of such impurities tends to deactivate the catalyst and/or increase the induction time. It is also preferred to conduct the polymerization under substantially anhydrous conditions.

The copolymers of the invention can be prepared by bulk polymerization. The polymerization can be carried out in the presence of an inert normally liquid organic vehicle such as, for example, aromatic hydrocarbons, e.g., benzene, toluene, xylene, ethylbenzene, and the like; oxygenated organic compounds such as anisole, the dimethyl and diethyl esters of ethylene glycol; normally liquid saturated hydrocarbons including open-chain, cyclic and alkyl-substituted-cyclic unsaturated hydrocarbons such as hexane, heptane, cyclohexane, alkylcyclohexanes, decahydronaphthalene and the like.

The polymerization process can be conducted in any convient manner, e.g., batch, semi-continuous, or continuous processes. The reaction vessel can be any equipment conventionally employed in the production of polymers. The monomeric reactants can be mixed in any order according to conventional polymerization techniques.

One aspect of this invention resides in the discovery that the above-disclosed polymer, when prepared in accordance with the methods discussed above and where epsilon caprolactone is present in a major amount, is a tough, elastomeric polymer at room temperatures, and temperatures up to about 100° F., but at temperatures substantially above that, and particularly, at "hot water" temperatures of about 115°-160° F., the polymer becomes moldable, such that it may be immersed in hot water and then shaped by the surgeon or other health practitioner to the exact shape desired for replacement by connective tissue, or the exact shape of the void formed, for example, after dental surgery. As noted, once implanted, the polymer implant will retain its shape until gradually replaced by regenerated tissue. This is of extreme importance in applications such as dental or oral surgery, or when involved with the repair or regeneration of tissue associated with joints and the like, where applied pressures would tend to permanently deform prior art implants.

As noted above, one particularly preferred embodiment of this invention comprises its use as an implant which not only provides for replacement by connective tissue, such as cartilage or bone, but also accelerates, or promotes, that regeneration. To this end, particularly in the regeneration of bone tissue, osteogenic material can be incorporated in the implant, preferably in the form of a powder or small particulate matter. Although the osteogenic material can be generally incoprorated in any amount up to a level where the physical properties of the copolymer of the implant are effected, a generally preferred range is 0–50%, by weight. Thus, B-tricalcium phosphate, hydroxyapetite, alumino-calcium-phosphorous oxide, allograft or autogenous bone chips, demineralized bone, and similar powdered or particulate material can be incorporated in the polymer. These materials may be incorporated either by providing it during polymerization, or, preferably, by introducing it after polymerization has occurred, but before the polymer has had a chance to harden to its final state. The presence of even minor amounts of osteogenic material dramatically improves the regeneration of bone material.

In yet another embodiment, where connective tissue is to be regenerated, the incorporation of chopped carbon fiber in the polymer implant of the claimed invention is contemplated. Chopped carbon fiber has been demonstrated, in other applications, to have superior soft tissue-regenerative utility, and its incorporation in an implant comprised of the polymer of this invention would secure similar improvement. Thus, the implant incorporating carbon fibers of the claimed invention exhibits a distinct advantage over prior art implants such as that suggested in U.S. Pat. No. 4,129,470, in that the chopped carbon fiber is incorporated in a bioabsorbable material, rather than one which is merely biocompatible, such as the PTFE of the reference. Implants of this type should, generally, be distinguished from those disclosed in the afore-referenced copending U.S. patent application Ser. No. 491,927, which is directed, in part, to an artificial ligament or tendon, which incorporates long strands of carbon fiber in a polymer similar to that employed herein, to function as the artificial member until regeneration of tissue can be achieved.

The advantages of the claimed invention over the prior art are immediately apparent. Unlike the collagen-based implants of the prior art, the implant disclosed herein is prepared from a polymer comprising solely synthetic materials, and accordingly, does not present the allergenic reaction problems encountered in the prior art. Similarly, sterility is no longer a concern, and sterile implants can be provided which have extraordinarily long shelf life. Further, the implants of the claimed invention, unlike those of the prior art, can be used where stability under applied pressure is necessary, such as an implant for a cavity or hole formed during dental or oral surgery. Yet, at the same time, the moldability of the implant is retained.

In employing this invention, a surgeon or related health technician would immerse a rough sample of the implant in hot water, or otherwise similarly heat it, to the temperature necessary to allow the implant to be easily molded by hand. While in this state, the implant would be molded to the exact dimension of the cavity or void to be filled, and then implanted into the patient. Of course, methods alternative to hot water immersion for heating the polymer to the necessary molding temperature could be employed. Substitutes including infrared heating, hot air, nichrome wire insertion and the like readily come to mind.

The above-disclosed invention has been described with respect to particular and preferred examples and embodiments. The substitution of equivalent materials, particularly with regard to the osteogenic material incorporated in the implant of this invention, and the ratios of materials involved, remains within the scope of the invention, which is defined by the claims set forth below.

What is claimed as new and desired to be secured by letters patents of the United States is:

1. A medical implant for the promotion of the regeneration of connective tissue, comprising:
    a shaped mass comprising a copolymer of epsilon caprolactone and lactide, said epsilon caprolactone being present in a major amount, further comprising an amount of osteogenic material effective to augment regeneration of soft or hard connective tissue incorporated in said mass,
    said shaped mass being moldable under mild pressure when heated to a temperature of about 115°-160° F., but resistant to permanent deformation under applied pressure at temperatures below about 110° F.

2. The medical implant of claim 1, wherein said epsilon caprolactone is present in a range of 60-95% by weight of the copolymer, and lactide is present in an amount of 40-5% by weight of the copolymer.

3. The medical implant of claim 1, wherein said epsilon caprolactone is present at about 75% by weight of the copolymer and said lactide is present at about 25% by weight of said copolymer.

4. The medical implant of claim 1, wherein said osteogenic material is present in an amount of up to 50% by weight of said copolymer.

5. The medical implant of claim 1, wherein said osteogenic material is in the form of particulate or powdered material.

6. The medical implant of claim 1, wherein said osteogenic material is selected from the group consisting of B-tricalcium phosphate, hydroxyapetite, alumino-calcium-phosphorous oxide, allograft bone chips, autogenous bone chips and demineralized bone.

7. The medical implant of claim 1, wherein said implant further comprises chopped carbon fiber incorporated in said shaped mass.

8. A method of promoting regeneration of soft or hard connective tissue in an animal, comprising:
    heating a mass of a copolymer comprising epsilon caprolactone in a major amount and lactide to a temperature of 115°-160° F. such that said mass becomes moldable, said mass further incorporating an amount of osteogenic material effective to augment connective tissue regeneration,
    molding said mass to the shape the tissue to be regenerated is desired to assume,
    implanting said molded mass in said animal in the area where said regeneration is desired, and
    allowing said mass to be replaced by regenerated tissue.

9. The method of claim 8, wherein said epsilon caprolactone is present in a range of 60-95% by weight of the copolymer, and lactide is present in a range of 40-5% by weight of the copolymer.

10. The method of claim 8, wherein said epsilon caprolactone is present at about 75% by weight of the copolymer and lactide is present at about 25% by weight of the copolymer.

11. The method of claim 8, wherein said osteogenic material is present in an amount up to 50% by weight of the polymeric mass.

12. The method of claim 8, wherein said osteogenic material is in the form of particulate or powdered material.

13. The method of claim 8, wherein said osteogenic material is selected from the group consisting of B-tricalcium phosphate, hydroxyapetite, alumino-calcium-phosphorous oxide, allograft bone chips, autogenous bone chips and demineralized bone.

14. The method of claim 8, wherein said polymeric mass further comprises chopped carbon fibers incorporated therein.

15. The method of claim 8, wherein said heating is achieved by immersion of said mass in hot water.

* * * * *